(12) United States Patent
Newman

(10) Patent No.: US 6,358,408 B1
(45) Date of Patent: *Mar. 19, 2002

(54) APPARATUS FOR THE ENHANCEMENT OF WATER QUALITY IN A SUBTERRANEAN PRESSURIZED WATER DISTRIBUTION SYSTEM

(76) Inventor: Michael R. Newman, 741 5th St. NW., Naples, FL (US) 34120

( * ) Notice: Subject to any disclaimer, the term of this patent is extended or adjusted under 35 U.S.C. 154(b) by 0 days.

This patent is subject to a terminal disclaimer.

(21) Appl. No.: 09/525,203

(22) Filed: Mar. 14, 2000

Related U.S. Application Data

(63) Continuation-in-part of application No. 09/096,626, filed on Jun. 12, 1998, now Pat. No. 6,035,704.

(51) Int. Cl.$^7$ ............................................. B01D 35/153
(52) U.S. Cl. ..................... 210/136; 137/236.1; 137/551; 210/85; 210/143; 210/170; 405/37; 405/39
(58) Field of Search .......................... 210/85, 94, 96.1, 210/97, 103, 136, 137, 143, 170, 194, 739, 745, 747; 73/53.01, 61.41, 168, 863.21, 863.71, 863.72; 137/1, 236.1, 551, 624.14, 624.2, 357, 561 R, 563, 5, 169–16; 405/36, 37, 39, 52, 128; 239/69, 70

(56) References Cited

U.S. PATENT DOCUMENTS

| | | | |
|---|---|---|---|
| 2,752,307 A | 6/1956 | Baran et al. ................. 204/195 |
| 3,592,212 A | 7/1971 | Schleimer ..................... 137/93 |
| 4,216,185 A * | 8/1980 | Hopkins ..................... 210/194 |
| 4,483,189 A | 11/1984 | Seal ............................. 73/155 |
| 4,639,718 A | 1/1987 | Gasper ........................ 340/603 |
| 5,002,428 A * | 3/1991 | Shettel ......................... 405/39 |
| 5,011,598 A | 4/1991 | Nathanson .................. 210/136 |
| 5,133,622 A * | 7/1992 | Hewlett ........................ 405/39 |
| 5,261,348 A | 11/1993 | Niehaus et al. ............... 166/64 |
| 5,324,665 A | 6/1994 | Lessard ........................ 436/55 |
| 5,332,494 A | 7/1994 | Eden et al. ................ 210/96.1 |
| 5,480,562 A | 1/1996 | Lemelson ................... 210/745 |
| 5,527,470 A | 6/1996 | Suda ........................... 210/739 |
| 5,540,845 A | 7/1996 | Blanchard et al. .......... 210/709 |
| 5,587,055 A | 12/1996 | Hartman et al. ................ 203/1 |
| 6,044,911 A * | 4/2000 | Haase ............................ 169/6 |

* cited by examiner

Primary Examiner—Joseph W. Drodge
(74) Attorney, Agent, or Firm—Akerman Senterfitt

(57) ABSTRACT

An apparatus for enhancing the water quality in a subterranean pressurized water system is disclosed and provides a discharge passage control via a valve that can be actuated electronically at the location of the valve or remotely. The discharge through the apparatus permits the flow of water in the subterranean pressurized water system and a corresponding discharge of contaminants and increased concentration of disinfectants supplied to the subterranean pressurized water system by the water system manager. The discharge can occur directly to a below ground drain such as a storm drain, sewer or drain field.

19 Claims, 2 Drawing Sheets

APPARATUS FOR THE ENHANCEMENT OF WATER QUALITY IN A SUBTERRANEAN PRESSURIZED WATER DISTRIBUTION SYSTEM

CROSS REFERENCE TO RELATED APPLICATIONS

This application is a continuation-in-part of application Ser. No. 09/096,626, now U.S. Pat. No. 6,035,704 filed Jun. 12, 1998.

STATEMENT REGARDING FEDERALLY SPONSORED RESEARCH OR DEVELOPMENT (Not Applicable)

FIELD OF THE INVENTION

The invention relates in general to water quality maintenance devices and more particularly to a water sampling and purging apparatus for automatically maintaining water quality in a low flow area of an underground water distribution system.

BACKGROUND OF THE INVENTION

As discussed in the above referenced parent application, traditional underground water distribution systems for residential and commercial areas often incorporate low flow or dead end portions by design. For instance, fire protection and land development codes often require oversized water mains for anticipated fire control and peak water demands. Such design features, although in the best interest of the community, have the effect of dramatically reducing water flow velocity and increasing water retention time within the water distribution system. The problem is further exacerbated by water distribution systems that experience large seasonal fluctuations in demand. These systems often experience additional reduction in water flow during non-seasonal periods of the year.

Low water flow conditions and corresponding increases in water retention time within portions of the water distribution system have the potential to degrade the chemical and microbiological quality of water transported through the distribution system. Degradation in water quality results from prolonged exposure to water system materials, internal sedimentation, and/or contaminant deposits within the piping system. Disinfectants are commonly used in an effort to control bacterial growth. However, as disinfectant residuals dissipate, bacterial regrowth occurs.

The Federal Safe Drinking Water Act requires that potable, or drinkable, water systems maintain minimum disinfection residual levels, to prevent the regrowth of bacteria. In fact, mandatory testing programs have been enacted to track compliance and identify potential health hazards. Water systems failing to adhere to regulatory or operational water quality standards are subject to regulatory enforcement action, public disclosure of health hazards, and increased public and regulatory scrutiny.

Corrosion rates in low flow and stagnant areas can escalate as chemical reactions and microbiological activity increase. Corrosive water tends to dissolve certain materials commonly used in the construction of water distribution systems. The two primary metals of concern are iron and lead. Iron is commonly found in piping system materials. Lead is commonly found in older water systems that have incorporated lead joints, lead composite pipes and/or brass fittings. Elevated iron concentrations can result in violations of drinking water standards. In both potable and non-potable water distribution systems, excessive concentrations of iron can result in staining of structure surfaces, fixtures and clothing.

Bacterial hazards also abound in low flow or dead end portions of water distribution systems. Increased bacterial concentrations result from reductions in disinfection residuals which retard or prevent the regrowth of such bacteria. Maintenance of adequate water system disinfection residuals is necessary to afford protection from accidental or intentional introduction of microbiological contaminants into the distribution system. Microbiological films, referred to in the art as bio-films, can form on water distribution system components where adequate disinfectant residual levels are not maintained. Removal of such films is expensive and time consuming.

Historically, water distribution system compliance with water quality regulatory standards has been evaluated through the collection of water samples. Presently, samples are collected from private plumbing systems and stationary water sampling stations installed along the water system distribution system. These designated sampling locations often produce test results that are either inaccurate or not representative of water quality throughout the water distribution system.

Historically, the primary means of addressing water quality degradation in low flow or dead end areas has been to dispatch workers, on a complaint-by-complaint basis, to manually purge the water from a problem area of the system. This method does not provide an adequate solution, since its success is contingent on financial and human resource availability.

Another approach that has been employed to supplement manual flushing operations has been the use of increased concentrations of disinfectant residuals, in an attempt to counteract the effects of disinfectant residual dissipation, which is a time dependent function of chemical and biological reactions. Using this approach, the disinfectant residual level of the entire system is increased or, alternatively, disinfectant booster stations are positioned at strategic areas along the water distribution system. However, due to suspicions that chlorine and other water-disinfecting chemicals may be carcinogenic, or responsible for creating carcinogenic substances during the disinfection process, there is a general consensus that dosage rates must be minimized. For instance, the Federal Safe Drinking Water Act is expected to establish a maximum limit of 4 mg/l for chlorine.

The prior art does not provide an adequate solution for addressing the aforementioned water quality degradation problems common at low flow and dead end areas of water distribution systems. The need for an adequate solution has been heightened as a result of an increase in the occurrence of known and suspected carcinogens in water distribution systems. Further, manual purging of low quality water causes excessive amounts of water to be discharged from the system thus making operation impractical in areas of poor drainage and high pedestrian/vehicular traffic. Moreover, prior art systems are generally shut down in subfreezing temperatures to protect system components from the expansion of freezing water.

Accordingly, what is needed is an apparatus capable of analyzing water quality and purging low quality water from low flow or dead end areas of water distribution systems. Various configurations can be provided to make the system adaptable to address particular drainage and traffic conditions. In some cases, it would be desirable for the aforementioned apparatus to have an internal control system capable of automatically monitoring water quality and, subsequently, purging low-quality water from the low flow area based upon user defined water quality limits. In some cases, it would be further desirable for the analytical and purging functions of the apparatus to be controllable by a remotely operated device. Additionally, it would also be desirable, in some cases, for the apparatus to provide a system for permitting operation of the apparatus in subfreezing temperatures and a device for preventing contaminants from entering the water distribution system.

SUMMARY OF THE INVENTION

The present invention provides an efficient and cost-effective means for maintaining water quality in low flow or dead end areas of an underground water distribution system. The invention generally embodies an apparatus for the automated analysis of water samples and purging of low quality water from such areas on an as-need basis. The apparatus greatly reduces present human resource requirements associated with performing these functions.

The apparatus is adapted for mounting above and below grade level, housing both above- and below-ground components. The major below-ground components of the apparatus can include the following: a water purging portion; a water inlet for introducing water from the water distribution system into the apparatus; a water carrier system for transporting water through the apparatus; an isolation valve for controlling the introduction of water into the apparatus; a flow control valve for controlling the flow of water through the apparatus; a freeze protection bypass system for permitting apparatus operation in subfreezing temperatures; a backflow prevention device for preventing contaminants from entering the water distribution system; a water quality monitoring system; and an electronic control system for activating, monitoring, and deactivating sampling and purging functions of the apparatus. Various optional components are also contemplated. For instance, radio and/or telephonic telemetry equipment may be housed in the below-ground portion of the apparatus for remote activation and deactivation of the apparatus.

The major above-ground components of the apparatus can include the following: a freeze protection bypass system; a backflow prevention device; a programming/data transmission access port; electrical/optical sensing devices; an external water quality sampling adapter; and a power source. The programming access port receives operational instructions from a remotely-held programming device. Various optional components are also contemplated. For instance, a turbine generator may be housed in the above-ground portion of the apparatus for recharging the power source.

Generally, instructions are communicated from a hand held remote control device through the programming access port to a programmable solenoid controller which is a subcomponent of the electronic control system. Preferably, the solenoid controller has date and time function capabilities such that a remote operator can program the apparatus to perform water purging functions at programmed times. The programmable solenoid also communicates with chemical, electronic and/or optical sensing devices, providing a means for purging based upon water quality parameters. Preferably, the power source comprises a rechargeable battery. The system can be housed in a water tight housing to prevent damage to internal components. The housing is specially designed to allow easy access to internal components. Preferably, bulky system components are stored below grade level in a specially designed water tight compartment, leaving only the relatively small aesthetically engineered portion of the housing above grade level. A protective cover can be used to house those components that are placed above ground.

One embodiment of a system for controlling and enhancing water quality in a subterranean pressurized water distribution system has been described in Applicant's application, U.S. Ser. No. 09/096,626, now U.S. Pat. No. 6,035,704, which is incorporated herein by reference. This embodiment provides for a downwardly directed discharge above ground. This discharge approach provides several advantages including the avoidance of dangers to passing pedestrians and traffic from high pressure discharge.

FIG. 1 discloses another embodiment for controlling and enhancing water quality in a subterranean pressurized water distribution system. The apparatus pictured in FIG. 1, a direct discharge subterranean discharge system, provides a discharge path that directs low quality water from a subterranean pressurized water distribution system to a below grade location such as a storm drain, sewer line or drain field. The apparatus is adapted for above and below ground, or grade level 180, mounting. As used herein, the term "upper portion" denotes structure located above grade level 180, and the term "lower portion" denotes structure located below grade level 180.

DETAILED DESCRIPTION OF PREFERRED EMBODIMENTS

Figure 1:
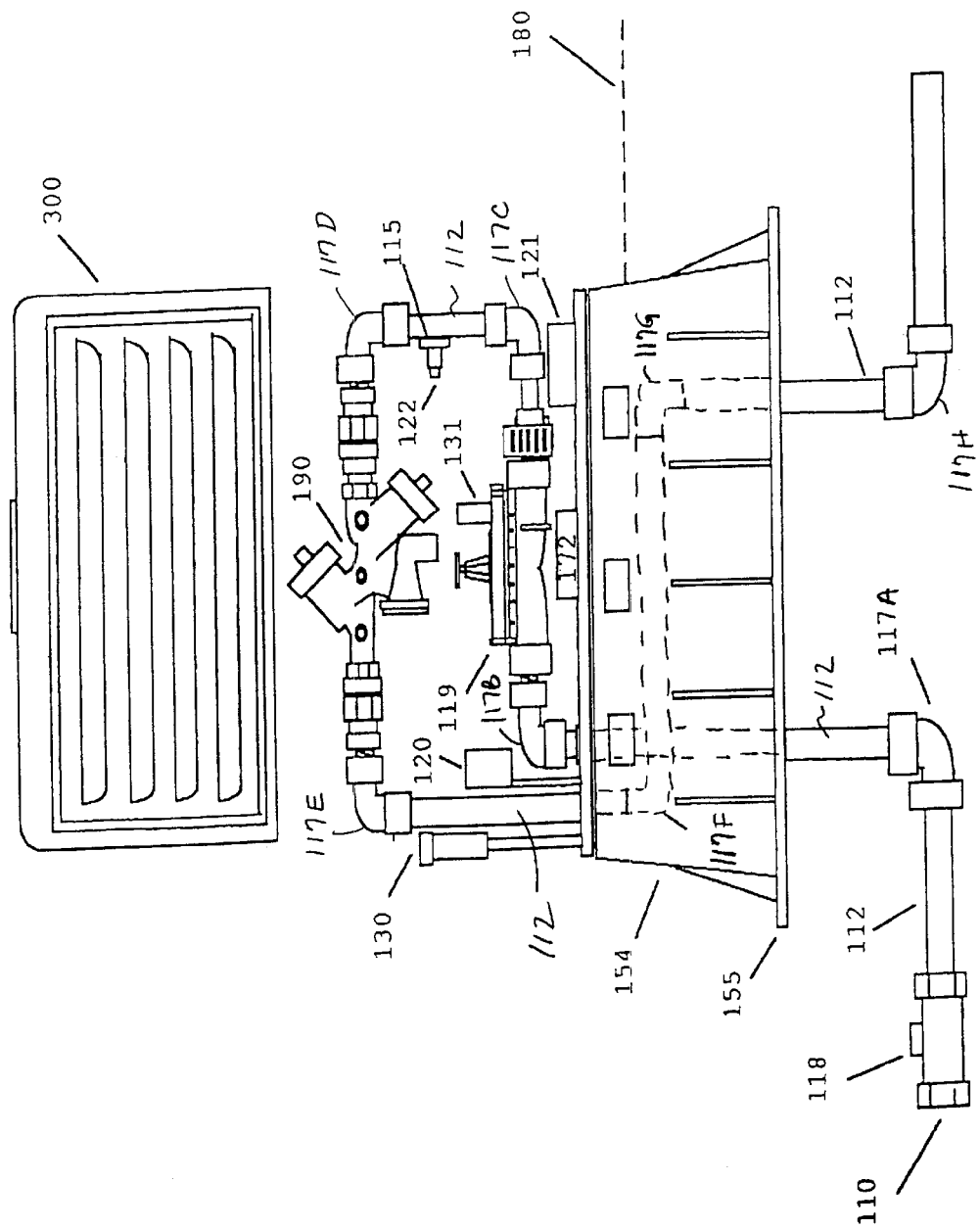
FIG. 1 illustrates an embodiment of a direct discharge subterranean discharge system in accordance with the principles of the present invention.

While the specification concludes with claims defining the features of the invention that are regarded as novel, it is believed that the invention will be better understood from consideration of the following description in conjunction with the drawing figures in which like reference numerals are carried forward.

In the preferred embodiment, the major components of the apparatus include the following: a housing; a water transport apparatus; a freeze protection bypass apparatus; a water flow control valve; a backflow prevention device; a programmable solenoid controller; a programming/data retrieval port; an electronic data control system; chemical, electronic and/or optical sensing devices; and a power source. Additionally, the apparatus may include a telephone and/or radio telemetry interface control system. The major system components each comprise subsystem components which cooperate to provide the advantages of the present invention.

Initially, water from a water distribution system (not shown) is received in water carrier piping 112 through water inlet 110. The dimensions and configuration of water inlet 110 are adapted for connection to the particular water distribution system piping. Water carrier piping 112 is made up of individual pipe segments. The carrier piping system is supported by various restraint mechanisms.

Water inlet 110 is connected to isolation valve 118. Isolation valve 118 controls the introduction of water into the apparatus. Under certain circumstances, it may be desirable to cut off water flow to the apparatus. For instance, isolation may be desirable when the apparatus is undergoing repair. Furthermore, if the apparatus is not equipped with a freeze protection bypass system, the isolation valve may be closed in subfreezing temperatures to isolate water from internal components thereby preventing component damage from the expansion of freezing water. Carrier piping 112 connects isolation valve 118 and carrier pipe elbow 117A. Carrier pipe elbow 117A transitions the carrier piping from a horizontal to vertical direction. Carrier piping 112 extends through a gasketed opening in lower housing support platform 155 and through another gasketed opening at the top of lower housing 154 and connects to carrier pipe elbow 117B. Carrier piping 112 is transitioned back to a horizontal direction by carrier pipe elbow 117B and connects to the inlet of water flow control valve 119.

Flow control valve 119 varies water flow through the apparatus thereby controlling the corresponding rate at which water is purged. In contrast to the manual methods of the prior art, the flow control valve of the present invention enables the discharge, or purging, of water at a controlled rate of flow over an extended period of time. As a result, the potential for land damage from erosion and flooding at the eventual draining site is greatly reduced. The outlet of flow control valve 119 is connected through carrier pipe elbows 117C and 117D and carrier piping 112 to the inlet of backflow prevention device 190. Backflow prevention device 190 is provided to prevent contaminants from entering the subterranean water distribution system through the apparatus. An auxiliary water sampling feature located between the outlet of flow control valve 119 and the inlet of backflow prevention device 190 is provided for performing manual on-site testing. The manual water sampling feature comprises water sampling adapter 122 which is configured to be adapted to carrier piping 112 through adapter 115. Preferably, water sampling adapter 122 is a quick connect/disconnect connector, as is well known in the art.

The carrier piping that is connected to the discharge side of backflow prevention device 190 through carrier pipe elbows 117E, 117F, 117G and 117H provides a discharge routing conduit for discharging low quality water to a subterranean drain system (not shown). As a result, this configuration allows low quality water to be purged subterraneously, thus permitting the apparatus to be installed in areas of inadequate surface drainage and/or high pedestrian/vehicular traffic. Further, this disposal option alleviates property and safety concerns associated with atmospheric flushing in such sensitive areas.

The apparatus can be fitted with a temperature activated freeze protection bypass system (not shown) that bypasses flow control valve 119 thereby enabling the apparatus to be operated in subfreezing temperatures. Since the present embodiment does not discharge water to the atmosphere, as opposed to the configuration disclosed in the parent application, the operational and safety hazards resulting from the formation of ice are eliminated. Thus, warmer water from the subterranean water distribution system can be flushed through the above grade components for their protection without activating flow control valve 119 when the water temperature in these components drops below a preset temperature.

The subterranean discharge configuration can incorporate all the remaining primary components of the above ground discharge embodiment of the parent application but does not require the water flow dissipater which is not required because low quality water is discharged below grade.

Specifically, programming/data retrieval port 130, such as a standard handset telephone jack, is integrated into the upper portion of the apparatus housing. Programming/data retrieval port 130 is adapted for receiving programming instructions from a remote hand-held programming device (not shown). For instance, the hand-held programming device could comprise a lap top computer. The hand-held electronic device communicates programming instructions (e.g., activation time) to programmable solenoid controller 131. Port 130 provides for bidirectional communication between the programming device and the programmable solenoid controller 131. As a result, stored data can be downloaded from the apparatus to the hand-held electronic device for analysis. Solenoid controller 131 is provided for activating and deactivating flow control valve 119. Therefore, instructions communicated from the remote programming interface function to control the activation and deactivation of flow control valve 119, thereby controlling the purging functions of the apparatus. For instance, programmable solenoid 131 can be programmed to activate flow control valve 119 at a specific time and date for a specified duration of time. Alternatively, chemical, electronic and/or optical sensing devices 120 provide a means for purging based on specific water parameters.

Chemical, electronic and/or optical sensing devices 120 are provided for measuring water quality parameters. In particular, the sensing devices are provided for measuring chemical and bacterial content of the water. The use of sensing devices for measuring water quality parameters is well known in the art. For instance, a water analyzing probe having a variety of sensors or electrodes for measuring various parameters of ground water is disclosed in U.S. Pat. No. 5,261,348 to Niehaus, et al. Sensing devices 120 could include pH electrodes, temperature sensors, or chlorine sensors, to name just a few. The sensing devices can be positioned at various locations within the apparatus. For instance, sensing devices 120 are positioned to test the water as it flows through carrier piping 112. Alternatively, sensors can be configured to provide continuous water sampling by connection, via sampling tubes, to water carrier piping 112 both before and after control valve 119. In this configuration, a minimal, continuous flow of water will exit through the apparatus. Through power cable interconnects, a signal from sensor device 120 can be communicated to data control system 121 and programming and data retrieval port 130. Subsequently, the monitoring signal from sensor device 120 can be used by control system 121 to activate control valve 119 through the programmable solenoid controller 131.

In the preferred embodiment of the present invention, the apparatus has electronic data control circuitry 121, including a microprocessor (not shown) for retrieving, storing, and transmitting data. Control circuitry 121 can be programmed through programming port 130 with a variety of instructions, including acceptable water parameter criteria. Programmed criteria stored by control circuitry 121 can be compared to measurement data communicated from sensing devices 120 to control circuitry 121. Control circuitry 121 has decision-making capabilities and, as a result, can signal solenoid controller 131 to activate or deactivate flow control valve 119, depending on the water quality test data.

In an alternative embodiment of the present invention, a telephone and/or radio telemetry interface control system 172 is housed in lower housing 154. These components provide a means for direct remote activation, monitoring and deactivation of the invention. The optional telemetry components can also be interfaced, either directly or indirectly, with programmable solenoid 131 to permit programming of the apparatus from remote locations.

The apparatus is powered by power source. Preferably, the power source comprises a battery, which may or may not be rechargeable. In an alternative embodiment of the present invention, at least one supplemental power source is provided. For instance, where power source is a rechargeable battery, at least one solar cell can be provided for recharging the battery. The optional solar cell provides low-power, continuous recharging capabilities to the battery, enabling increased operating intervals between replacement or supplemental external recharging.

Furthermore, an internal water-powered turbine electric power generator can be provided. Electric turbine generator uses the stored kinetic energy in the pressurized water being discharged to rotate an in-line turbine, which in turn operates an electrical generator (not shown). The electrical generator is capable of meeting the electrical requirements of the invention's various electrical and electronic configurations. The turbine generator is also capable of recharging optional back-up batteries or other supplemental battery power sources.

The apparatus housing has other various features which will now be described. Preferably, lower housing 154 protects the below grade components from the elements. Additionally, lower housing support platform 155 has a larger area than the remainder of the apparatus which allows for distribution of the weight of the apparatus over a greater surface area thereby reducing the unit loading on the load bearing surface and minimizing the potential for settling. Lower housing 154 can be provided with an emergency relief valve. In the event of a leak or other material failure in the pressurized portion of the apparatus, i.e., in lower housing 154, an emergency relief valve provides a means for pressure relief thereby minimizing the potential for damage to electrical and electronic components housed in lower housing 154. Protective cover 300 houses the above grade components.

Figure 2:
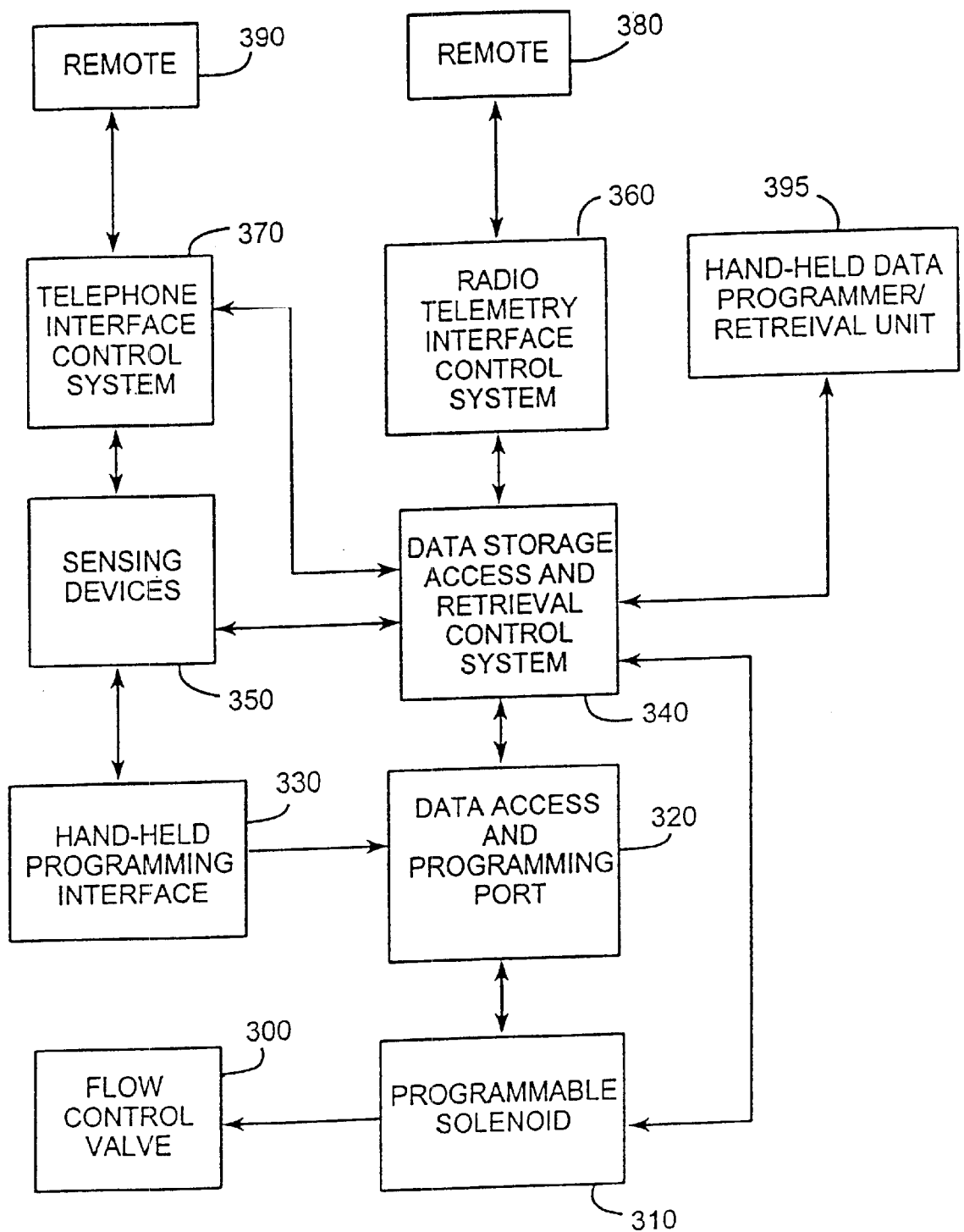
FIG. 2 is a block diagram illustrating the interaction of the major system components of the apparatus of the present invention.

Referring now to FIG. 2, although the interaction of the various components of the apparatus of the instant invention has now been described in substantial detail, a block diagram summarizing this interaction is provided. At a minimum, hand-held programming device/interface 330, programming & data retrieval port 320, programmable solenoid 310 and flow control valve 300 are provided. Operating instructions are communicated from device 330, through port 320, to programmable solenoid 310. Based upon the instructions received by solenoid 310, flow control valve 300 may be activated or deactivated for a period of time.

The preferred embodiment of the present invention further comprises central data control system 340 and sensing devices 350. In this embodiment, water quality criteria can be communicated from control system 340 to sensing devices 350, while specific water quality test data can be communicated from sensing devices 350 to control system 340. Based upon the water quality criteria and test data, control system 340 can signal programmable solenoid 310, either directly or through port 320, to activate or deactivate flow control valve 300. Hand-held programming/data retrieval unit 395, which preferably comprises a portable computer, communicates bidirectionally with data control system 340.

Optionally, telephone or radio telemetry interfaces 360, 370 can be integrated into the system of the instant invention, as a means for providing bidirectional communication with remotely operated devices 380, 390. For instance, remote devices 380 and 390 may be used to directly activate or deactivate the purging functions of the apparatus from afar, by communicating, through interfaces 360 and 370, respectively, with central control system 340.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. An apparatus for the enhancement of water quality in a subterranean pressurized water distribution system, said apparatus comprising:

a flow controlled passage for pressurized water having an inlet adapted for fluid connection to said subterranean pressurized water distribution system, said flow controlled passage having a conduit for directing pressurized water received in said inlet to a routing conduit for redirecting said pressurized water subterraneously, said routing conduit having an outlet adapted for fluid connection to a drain system for receiving said pressurized water, whereby atmospheric discharge of said pressurized water and its associated dangers are avoided;

a flow control valve disposed along said flow controlled passage for permitting and prohibiting the flow of pressurized water through the flow controlled passage;

programmable electronic control circuitry for controlling the flow of pressurized water through said flow controlled passage by activating and deactivating the flow control valve, said system including a programmable microprocessor system for storing instructions for activating and deactivating the flow control valve; and at least one programming interface operatively connected to the microprocessor system for inputting electronic information to be stored and processed in said microprocessor system for activating and deactivating said flow control valve, further comprising a housing enclosing said microprocessor system, flow control valve and at least a portion of said flow controlled passage for protecting against environmental factors external to the housing.

2. The apparatus according to claim 1, wherein said routing conduit extends above ground.

3. The apparatus according to claim 1, wherein said drain system is a storm drain.

4. The apparatus according to claim 1, wherein said drain system is a sewer line.

5. The apparatus according to claim 1, wherein said drain system is a drain field.

6. The apparatus according to claim 1, wherein said at least one programming interface includes a port for removably interfacing with a portable programming device for programming said programmable electronic control circuitry.

7. The apparatus according to claim 6, wherein the port permits bidirectional transmission of electronic information between the programmable electronic control circuitry and the portable programming device temporarily attached to the port.

8. The apparatus according to claim 1, further comprising at least one of chemical, electronic and optical sensing devices operatively connected to said at least one programming interface and providing data signals to the programmable electronic control circuitry, said programmable electronic control circuitry controlling said flow control valve for permitting and prohibiting said flow and discharge of said pressurized water, said flow control valve controlling flow responsive to said data signals.

9. The apparatus according to claim 8, wherein said at least one sensing device communicates bi-directionally with said programmable electronic control circuitry.

10. The apparatus according to claim 1, further comprising at least one interface control system from the group of a telephone interface control system and a radio telemetry interface control system, said at least one interface control system communicating bi-directionally with said programmable electronic control circuitry through said at least one programming interface.

11. The apparatus according to claim 1, further comprising a water sampling adapter fluidly communicating with the flow controlled passage for obtaining water samples.

12. The apparatus according to claim 1, wherein said flow control valve has means for adjusting the flow rate of water through said flow controlled passage.

13. An apparatus for the enhancement of water quality in a subterranean pressurized water distribution system, said apparatus comprising:

a flow controlled passage for pressurized water having an inlet adapted for fluid connection to said subterranean pressurized water distribution system, said flow controlled passage having a conduit for directing pressurized water received in said inlet to a routing conduit for redirecting said pressurized water subterraneously, said routing conduit having an outlet adapted for fluid connection to a drain system for receiving said pressurized water, whereby atmospheric discharge of said pressurized water and its associated dangers are avoided;

a flow control valve disposed along said flow controlled passage for permitting and prohibiting the flow of pressurized water through the flow controlled passage;

programmable electronic control circuitry for controlling the flow of pressurized water through said flow controlled passage by activating and deactivating the flow control valve, said system including a programmable microprocessor system for storing instructions for activating and deactivating the flow control valve; and at least one programming interface operatively connected to the microprocessor system for inputting electronic information to be stored and processed in said microprocessor system for activating and deactivating said flow control valve, further comprising a backflow prevention device connected between said drain system and said flow control valve for preventing contaminants from entering said subterranean pressurized water distribution system, wherein said backflow prevention device is disposed above ground, further comprising a protective cover enclosing said routing conduit, flow control valve and backflow prevention device for protecting against environmental factors external to said protective cover.

14. The apparatus according to claim 13, wherein said routing conduit extends above ground.

15. The apparatus according to claim 13, further comprising a backflow prevention device connected between said drain system and said flow control valve for preventing contaminants from entering said subterranean pressurized water distribution system.

16. The apparatus according to claim 15, wherein said backflow prevention device is disposed above ground.

17. The apparatus according to claim 13, wherein said drain system is a storm drain.

18. The apparatus according to claim 13, wherein said drain system is a sewer line.

19. The apparatus according to claim 13, wherein said drain system is a drain field.

* * * * *

UNITED STATES PATENT AND TRADEMARK OFFICE
CERTIFICATE OF CORRECTION

PATENT NO. : 6,358,408 B1
DATED : March 19, 2002
INVENTOR(S) : Newman

It is certified that error appears in the above-identified patent and that said Letters Patent is hereby corrected as shown below:

<u>Column 8,</u>
Line 59, replace "temporarily attached to" with -- removably interfaced with --.

Signed and Sealed this

Twenty-fourth Day of September, 2002

Attest:

Attesting Officer

JAMES E. ROGAN
*Director of the United States Patent and Trademark Office*